US009035011B2

(12) United States Patent
Ferenz et al.

(10) Patent No.: US 9,035,011 B2
(45) Date of Patent: May 19, 2015

(54) MODIFIED ALKOXYLATION PRODUCTS HAVING AT LEAST ONE NON-TERMINAL ALKOXYSILYL GROUP AND A PLURALITY OF URETHANE GROUPS, AND THEIR USE

(71) Applicant: Evonik Goldschmidt GmbH, Essen (DE)

(72) Inventors: Michael Ferenz, Essen (DE); Bastian Matthias Brugger, Oberhausen (DE); Matthias Lobert, Essen (DE); Volker Zellmer, Bottrop (DE); Frank Schubert, Neukirchen-Vluyn (DE); Wilfried Knott, Essen (DE); Melanie Roessing, Oberhausen (DE)

(73) Assignee: Evonik Goldschmidt GmbH, Essen (DE)

(*) Notice: Subject to any disclaimer, the term of this patent is extended or adjusted under 35 U.S.C. 154(b) by 50 days.

(21) Appl. No.: 13/793,356

(22) Filed: Mar. 11, 2013

(65) Prior Publication Data
US 2013/0237616 A1 Sep. 12, 2013

(30) Foreign Application Priority Data
Mar. 9, 2012 (DE) .......... 10 2012 203 737

(51) Int. Cl.
*C08G 18/50* (2006.01)
*C08G 18/48* (2006.01)
*C08G 18/28* (2006.01)
*C08G 18/06* (2006.01)
*C08G 18/38* (2006.01)
*C08G 65/22* (2006.01)
*C08G 65/00* (2006.01)
*C07F 7/18* (2006.01)

(52) U.S. Cl.
CPC ............ *C08G 18/5096* (2013.01); *C08G 18/48* (2013.01); *C08G 18/2815* (2013.01); *C08G 18/06* (2013.01); *C08G 18/38* (2013.01); *C08G 18/50* (2013.01); *C08G 65/22* (2013.01); *C08G 18/28* (2013.01); *C07F 7/1804* (2013.01); *C08G 65/00* (2013.01)

(58) Field of Classification Search
None
See application file for complete search history.

(56) References Cited

U.S. PATENT DOCUMENTS

| 3,278,457 | A | 10/1966 | Milgrom |
|---|---|---|---|
| 3,278,458 | A | 10/1966 | Belner |
| 3,278,459 | A | 10/1966 | Herold |
| 3,427,256 | A | 2/1969 | Milgrom |
| 3,427,334 | A | 2/1969 | Belner |
| 3,427,335 | A | 2/1969 | Herold |
| 5,306,737 | A | 4/1994 | Burkhart et al. |
| 5,321,051 | A | 6/1994 | Burkhart et al. |
| 5,357,018 | A | 10/1994 | Burkhart et al. |
| 5,371,161 | A | 12/1994 | Knott et al. |
| 5,455,367 | A | 10/1995 | Klein et al. |
| 5,470,813 | A | 11/1995 | Le-Khac |
| 5,475,127 | A | 12/1995 | Klein et al. |
| 5,482,908 | A | 1/1996 | Le-Khac |
| 5,565,194 | A | 10/1996 | Burkhart et al. |
| 5,777,177 | A | 7/1998 | Pazos |
| 6,291,622 | B1 | 9/2001 | Droese et al. |
| 6,307,082 | B1 | 10/2001 | Klein et al. |
| 6,858,663 | B2 | 2/2005 | Knott et al. |
| 7,018,458 | B2 | 3/2006 | Knott et al. |
| 7,125,585 | B2 | 10/2006 | Dudzik et al. |
| 7,157,541 | B2 | 1/2007 | Knott et al. |
| 7,196,153 | B2 | 3/2007 | Burkhart et al. |
| 7,312,364 | B2 | 12/2007 | Cramers et al. |
| 7,598,334 | B2 | 10/2009 | Ferenz et al. |
| 7,605,284 | B2 | 10/2009 | Brueckner et al. |
| 7,612,158 | B2 | 11/2009 | Burkhart et al. |
| 7,612,159 | B2 | 11/2009 | Burkhart et al. |
| 7,619,035 | B2 | 11/2009 | Henning et al. |
| 7,635,581 | B2 | 12/2009 | Ferenz et al. |
| 7,645,848 | B2 | 1/2010 | Knott et al. |
| 7,754,778 | B2 | 7/2010 | Knott et al. |
| 7,776,989 | B2 | 8/2010 | Ferenz et al. |
| 7,825,205 | B2 | 11/2010 | Knott et al. |
| 7,825,206 | B2 | 11/2010 | Neumann et al. |
| 7,825,207 | B2 | 11/2010 | Ferenz et al. |
| 7,825,209 | B2 | 11/2010 | Knott et al. |
| 7,834,122 | B2 | 11/2010 | Ferenz et al. |
| 7,964,694 | B2 | 6/2011 | Ferenz et al. |
| 8,030,366 | B2 | 10/2011 | Ferenz et al. |
| 8,058,388 | B2 | 11/2011 | Sellmann et al. |
| 8,138,294 | B2 | 3/2012 | Henning et al. |
| 8,172,936 | B2 | 5/2012 | Herrwerth et al. |
| 8,198,473 | B2 | 6/2012 | Ferenz et al. |
| 8,211,972 | B2 | 7/2012 | Meyer et al. |
| 8,268,939 | B2 | 9/2012 | Ebbrecht et al. |
| 8,283,422 | B2 | 10/2012 | Schubert et al. |

(Continued)

FOREIGN PATENT DOCUMENTS

| DE | 698 31 518 | 6/2006 |
|---|---|---|
| DE | 10 2006 054 155 | 5/2008 |

(Continued)

OTHER PUBLICATIONS

European Search Report, EP 13 15 8284, mailed May 31, 2013.
Isomer definitions given by Professor Kazmaier of the Saarland University, e.g. http://www.uni-saarland.de/fak8/kazmaier/PDF_files/vorlesungen/Stereochemic%20Strassb%20Vorlage.pdf and English translation thereof.
"Dictionary of Natural Products", Chapman and Hall/CRC Press, Taylor and Francis Group, online version of 2011: http://dnp.chemnetbase.com/.

*Primary Examiner* — Marc Zimmer
(74) *Attorney, Agent, or Firm* — Frommer Lawrence & Haug LLP

(57) ABSTRACT

Alkoxylation products, their preparation, compositions comprising these alkoxylation products, and the use thereof as or for producing adhesives and sealants.

13 Claims, No Drawings

(56) References Cited

U.S. PATENT DOCUMENTS

| | | | |
|---|---|---|---|
| 8,309,664 B2 | 11/2012 | Knott et al. | |
| 8,309,673 B2 | 11/2012 | Schubert et al. | |
| 8,324,325 B2 | 12/2012 | Knott et al. | |
| 8,334,355 B2 | 12/2012 | Henning et al. | |
| 2002/0161158 A1 | 10/2002 | Burkhart et al. | |
| 2007/0059539 A1 | 3/2007 | Doehler et al. | |
| 2007/0128143 A1 | 6/2007 | Gruning et al. | |
| 2007/0197678 A1 | 8/2007 | Cavaleiro et al. | |
| 2009/0075096 A1* | 3/2009 | Butikofer et al. | 428/447 |
| 2009/0137752 A1 | 5/2009 | Knott et al. | |
| 2010/0022435 A1 | 1/2010 | Henning et al. | |
| 2010/0034765 A1 | 2/2010 | Herrwerth et al. | |
| 2010/0036011 A1 | 2/2010 | de Gans et al. | |
| 2010/0041910 A1 | 2/2010 | Schubert et al. | |
| 2010/0071849 A1 | 3/2010 | Knott et al. | |
| 2010/0081781 A1 | 4/2010 | Schubert et al. | |
| 2010/0210445 A1 | 8/2010 | von Rymon Lipinski et al. | |
| 2010/0248325 A1 | 9/2010 | Eckstein et al. | |
| 2010/0249339 A1 | 9/2010 | Henning et al. | |
| 2010/0266518 A1 | 10/2010 | Springer et al. | |
| 2010/0298455 A1 | 11/2010 | Henning et al. | |
| 2011/0021693 A1 | 1/2011 | Henning et al. | |
| 2011/0042004 A1* | 2/2011 | Schubert et al. | 156/329 |
| 2011/0046305 A1* | 2/2011 | Schubert et al. | 524/869 |
| 2011/0070175 A1 | 3/2011 | Herrwerth et al. | |
| 2011/0091399 A1 | 4/2011 | Meyer et al. | |
| 2011/0230619 A1 | 9/2011 | Kuppert et al. | |
| 2011/0230633 A1 | 9/2011 | Ferenz et al. | |
| 2011/0301254 A1 | 12/2011 | Knott et al. | |
| 2012/0010302 A1 | 1/2012 | Hartung et al. | |
| 2012/0027704 A1 | 2/2012 | Henning et al. | |
| 2012/0028022 A1 | 2/2012 | Brugger et al. | |
| 2012/0029090 A1 | 2/2012 | Brugger et al. | |
| 2012/0037036 A1 | 2/2012 | Veit et al. | |
| 2012/0046486 A1 | 2/2012 | Henning et al. | |
| 2012/0067520 A1 | 3/2012 | Schubert et al. | |
| 2012/0068110 A1 | 3/2012 | Schubert et al. | |
| 2012/0071564 A1 | 3/2012 | de Gans et al. | |
| 2012/0097883 A1 | 4/2012 | Henning et al. | |
| 2012/0168664 A1 | 7/2012 | Maurer et al. | |
| 2012/0190760 A1 | 7/2012 | Henning et al. | |
| 2012/0282210 A1 | 11/2012 | Henning et al. | |
| 2012/0294819 A1 | 11/2012 | Herrwerth et al. | |
| 2012/0296125 A1 | 11/2012 | Schubert et al. | |
| 2012/0308494 A1 | 12/2012 | Schubert et al. | |
| 2013/0041102 A1 | 2/2013 | Albrecht et al. | |
| 2013/0041115 A1 | 2/2013 | Knott et al. | |

FOREIGN PATENT DOCUMENTS

| | | |
|---|---|---|
| DE | 10 2009 022 630 | 12/2010 |
| DE | 10 2010 038 774 | 2/2012 |
| EP | 0 981 407 | 3/2000 |
| EP | 1 017 738 | 7/2000 |
| EP | 1 474 464 | 11/2004 |
| EP | 2 093 244 | 8/2009 |
| EP | 2093244 | 8/2009 |
| EP | 2415797 | 2/2012 |
| JP | 0762222 | 3/1995 |
| JP | 0912861 | 1/1997 |
| JP | 0912863 | 1/1997 |
| WO | WO 98/52689 | 11/1998 |
| WO | WO 99/14258 | 3/1999 |
| WO | WO 03/066706 | 8/2003 |
| WO | WO 2005/003201 | 1/2005 |
| WO | WO 2005/100482 | 10/2005 |
| WO | WO 2006/002807 | 1/2006 |
| WO | WO 2010/136280 | 12/2010 |

* cited by examiner

MODIFIED ALKOXYLATION PRODUCTS HAVING AT LEAST ONE NON-TERMINAL ALKOXYSILYL GROUP AND A PLURALITY OF URETHANE GROUPS, AND THEIR USE

The present application claims priority from German Patent Application No. DE 10 2012 203 737.3 filed on Mar. 9, 2012, the disclosure of which is incorporated herein by reference in its entirety.

1. FIELD OF THE INVENTION

The invention relates to alkoxylation products, their preparation, compositions comprising the alkoxylation products of the invention, and the use thereof as or for producing adhesives and sealants.

It is noted that citation or identification of any document in this application is not an admission that such document is available as prior art to the present invention.

Conventional polyether alcohols, often also referred to simply for short as polyethers and composed chiefly of propylene oxide and ethylene oxide, are well established and are produced industrially in large quantities. Among other applications, they serve, through reaction with polyisocyanates, as starting compounds for producing polyurethanes, or else for producing surfactants.

Organic alkoxysilane compounds such as 3-glycidyloxypropyl-trimethoxysilane or -triethoxysilane, which are available for example under the trade names DYNASYLAN® GLYMO or DYNASYLAN® GLYEO (trade marks of Evonik Degussa GmbH), enter into the production of organically modified networks in the context of the sol-gel process, which serves as a key operation in the production of nanocomposites that provide coating systems with enhanced properties in respect of hardness, scratch and abrasion resistance, temperature resistance, and also solvent and acid resistance. Alkoxysilane compounds, moreover, are employed diversely in sealants and adhesives and also, generally, as reactive adhesion promoters and primers for various substrates such as metals, glass and glass fibres/glass fabrics for fibre-reinforced composite materials and for the surface treatment of, for example, pigments and fillers in coating materials.

There has been no lack of efforts made to improve the profiles of properties of alkoxysilane compounds by means of chemical modifications, in order to open up even further fields of application to this significant product class. For instance, it is known from the literature that the profile of properties of alkoxylation products (polyethers) can be combined with those of crosslinkable compounds carrying alkoxysilyl groups especially. For instance, DE 69831518 T2 is based on the modification of polyether alcohols with, for example, alkoxysilanes which carry isocyanate groups, with urethanizing linkage. Additionally selected for alkoxysilyl modification is the hydrosilylating attachment of alkoxymonohydridosilanes onto polyetherols that have been modified beforehand with olefinically unsaturated end groups.

Specifications JP 09012863, JP 09012861 and JP 07062222 claim a process for producing polyetherols equipped exclusively terminally with hydrolysable trialkoxylsilyl functions, such as glycerol polyetherols, for example, which are first prepared via DMC catalysis and are then converted, by addition of alkali metal alkoxide and aryl chloride into the corresponding allyl ethers, and subsequently, by hydrosilylation, catalysed by platinum metal, into the alkoxysilyl-terminated target products.

All of the processes described in the prior art are therefore suitable only for the preparation of polyoxyalkylene compounds modified exclusively terminally with trialkoxysilyl groups, and not for the single and/or multiple modification of polyether chains with trialkoxy functions within the sequence of oxyalkylene units as well.

According to EP 2 093 244 it was possible for the first time to prepare alkoxylation products which carry alkoxysilyl groups and are notable for the fact that, in contrast to the prior art known until that date, the alkoxysilyl groups are distributed randomly or in blocks along the polyether chain, and are not just located at the termini of the chain. These compounds, furthermore, are notable for a terminal OH group, which is a consequence of the reaction.

The presence of the OH group and the hydrolysis-sensitive alkoxysilyl groups in one molecule are the bases for the intrinsic reactivity of the compounds and ready crosslinkability with formation of three-dimensional polymeric networks. Experiments, however, have also shown that the reactivity of the OH group may be too high.

DE 10 2010 038774 describes non-hydroxylated polymers which contain alkoxysilyl groups and which consist of polyether blocks and urethane units. The breaking stress of the process products is inadequate.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is an object of the present invention, therefore, to provide compounds which, after they have cured, exhibit an increased breaking stress relative to alkoxysilyl-containing polymers of the prior art.

Surprisingly it has been found that compounds containing the reaction products with polyfunctional isocyanates as defined below achieve this object.

The present invention accordingly provides alkoxylation products as described in the claims.

The present invention further provides a process for preparing alkoxylation products of the invention, which is characterized in that in a first reaction step (a) polyethers PE are reacted with diisocyanates and in a second reaction step (b) the product and/or the product mixture of the first reaction step (a) is reacted with a molecule of the formula H-M. Polyethers PE, diisocyanates and molecules of the formula H-M are defined below.

Likewise provided by the present invention are compositions comprising at least one of the alkoxylation products of the invention, alone or in mixtures with further, optionally curable substances.

The present invention further provides for the use of the alkoxylation products of the invention, and also of the products of the process of the invention, and also of the compositions of the invention comprising the alkoxylation products of the invention.

One advantage of the invention is that the alkoxylation products of the invention, and also products of the process of the invention, have excellent storage stability. It is likewise advantageous that the compositions of the invention comprising the alkoxylation products of the invention, and also products of the process of the invention, are outstandingly storage-stable in the absence of water and/or moisture following addition of a curing catalyst.

Another advantage of the invention is that the alkoxylation products of the invention, and also products of the process of the invention, do not emit any toxic substances.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The alkoxylation products of the invention, the products of the process of the invention, the processes of the invention for preparing the compositions, and also the inventive use thereof, are described by way of example below, without any intention that the invention should be confined to these exemplary embodiments. Where ranges, general formulae or classes of compound are specified below, they should be taken to encompass not only the corresponding ranges or groups of compounds that are explicitly stated, but also all sub-ranges and sub-groups of compounds which can be obtained by extracting individual values (ranges) or compounds. Where the present description cites documents, the intention is that the content of these documents should in its entirety form part of the disclosure content of the present invention. Where content figures (ppm or %) are given below or above, they are, unless otherwise indicated, figures in % by weight or ppm by weight (wppm). In the case of compositions, the content figures, unless otherwise indicated, are based on the overall composition. Where averages are given below, they are, unless otherwise indicated, the number average. Where molar masses are used, they are, unless expressly noted otherwise, weight-average molar masses Mw with the unit g/mol. Where measurement values are indicated below, then these measurement values, unless otherwise indicated, have been ascertained at a pressure of 1013.25 hPa and at a temperature of 25° C.

The definitions below in some cases include further terms, which are used equivalently and synonymously with the term defined.

The word fragment "poly" in connection with this invention encompasses not only exclusively compounds having at least 3 repeating units of one or more monomers in the molecule, but also, more particularly, those compositions of compounds which exhibit a molecular weight distribution and possess an average molecular weight of at least 200 g/mol. This definition takes account of the fact that, within the field of art in question, it is usual to identify such compounds as polymers even when they do not appear to satisfy a polymer definition along the lines of OECD or REACH directives.

Wherever molecules or molecular fragments have one or more stereocentres or can be differentiated into isomers on the basis of symmetries, or on the basis of other effects, such as restricted rotation, for example, all of the possible isomers are included by the present invention.

Isomers are known to the skilled person; the reader is referred particularly to the definitions given by Professor Kazmaier of the Saarland University, e.g. http://www.uni-saarland.de/fak8/kazmaier/PDF_files/vorlesungen/Stereochemie % 20Strassb % 20Vorlage.pdf.

Where reference is made within this invention to natural substances, such as lactate, for example, the intention in principle is to refer to all the isomers, preferably those isomers that occur naturally in each case, and hence, in the instants cited here, L-lactate.

With regard to the definition of natural substances, refer to the "Dictionary of Natural Products", Chapman and Hall/CRC Press, Taylor and Francis Group, as for example in the online version of 2011: http://dnp.chemnetbase.com/.

The various fragments in the formulae (Ia) and (II) below may be distributed statistically. Statistical distributions may have a blockwise construction with an arbitrary number of blocks and an arbitrary sequence, or may be subject to a randomized distribution; they may also be constructed in alternation or else may form a gradient over the chain; in particular they may also form all hybrid forms in which, optionally, groups with different distributions may follow one another. The formulae (I), (Ia) and (II) describe polymers which have a molar weight distribution. The indices therefore represent the numerical average over all of the monomer units.

The indices a, b, c, d, e, f, g, h, j, k, l, m, n, o, p, q, r, s, t, u and v that are used in the formulae, and also the value ranges for the indices specified, may be understood as average values of the possible statistical distribution of the structures and/or mixtures thereof that are actually present. This applies even to those structural formulae which as such, per se, are reproduced exactly, such as for formula (Ia) and (II), for example.

The alkoxylation products of the invention which comprise the structural elements of the formula (I)

$$M_iD_jT_kQ_lUR_uAP_v \qquad \text{formula (I)}$$

are distinguished by the fact that the fragments M, D, T and Q are linked not to one another but instead with one another via the groups UR and/or AP, and the groups UR and AP are not linked to one another but instead, accordingly, are linked with one another via the fragments D, T or Q.

With regard to the indices, i=2 to 16, preferably greater than 2 to 12, j=1 to 10, preferably 1.2 to 8, more preferably 1.5 to 6, very preferably greater than or equal to 2 k=0 to 6, preferably greater than 0 to 4, more particularly 0.5 to 2, l=0 to 4, preferably greater than 0 to 3, more particularly 0.5 to 2, j+k is greater than or equal to 1.5, preferably greater than or equal to 2, u=2 to 17, preferably greater than 2 to 15, more preferably 2.5 to 10, more particularly 3 to 8, v=0 to 6, preferably greater than 0 to 4, more particularly 0.1 to 2.

M independently at each occurrence is a hydrocarbon residue which carries an oxygen radical and has a minimum numerical molar mass of 88 g/mol, and which may optionally be interrupted by heteroatoms,
preferably a hydrocarbon residue of the formula $$C_oH_{2o+1}-O-(C_mH_{2m}-O)_n-(CH_2CH_2-O-)_p-(CH_2CH(CH_3)O)_r-, \text{ where}$$

o=1 to 36, including for example 5 to 16 or 8 to 11, preferably 2 to 20, more preferably 3 to 16, more particularly 4 to 12,
m=3 to 6, n=0 to 50, p=0-50,
r=2 to 40, preferably 3 to 30, more particularly 4 to 20;
more preferably the hydrocarbon residue is a polyether consisting of
polypropylene oxide prepared starting from butanol; more particularly, M is $C_4H_9O[CH_2CH(CH_3)O]_{5.3}$—
or M is a radical of the formula (Ia)

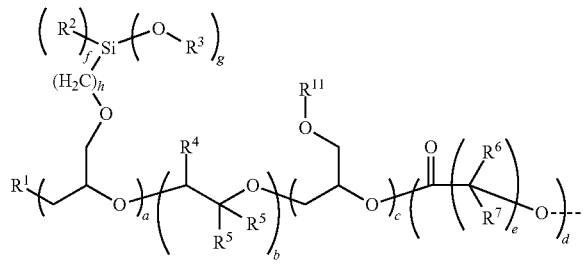

formula (Ia)

wherein
a=0 to 1000, preferably 1 to 100 or greater than 1 to 100, more preferred 2 to 50, with the proviso that the sum of index a in formula (II) and formula (Ia) must be greater than or equal to 1,
b=0 to 1000, preferably 1 to 500, more preferred greater 1 to 400,
c=0 to 1000, preferably 1 to 100 or greater than 1 to 100, more preferred 0 to 50,
d=0 to 1000, preferably 1 to 100 or greater than 1 to 100, more preferred 0 to 50,
with the proviso that the groups having the indices a, b, c and d are freely permutable over the molecular chain,
e=1 to 10,
g+f=3 and g is at least 1,
h=0 to 10, preferably 1 to 10, more preferably 3
and with the proviso that the different monomer units both of the fragments having the indices a, b, c and d and of the polyoxyalkylene chain of the substituent $R^1$ may be constructed in blocks with one another or else may be subject to a statistical distribution and, moreover, are freely permutable with one another,
and wherein
$R^1$=independently at each occurrence a saturated or unsaturated, linear or branched organic hydrocarbon residue which may be further substituted and contain O, S and/or N as heteroatoms,
the hydrocarbon residue preferably containing 4 to 400 carbon atoms,
$R^2$=independently at each occurrence an alkyl group having 1 to 8 carbon atoms, more particularly methyl or ethyl,
$R^3$=independently at each occurrence an alkyl group having 1 to 8 carbon atoms, more particularly methyl, ethyl, propyl, isopropyl, $R^4$=independently at each occurrence a hydrogen radical or an alkyl group having 1 to 8 carbon atoms,
preferably hydrogen, methyl or ethyl, more preferably hydrogen,
$R^5$=independently at each occurrence a hydrogen radical, an alkyl group having 1 to 20 carbon atoms or an aryl or alkaryl group,
preferably hydrogen, methyl, ethyl, octyl, decyl, dodecyl, phenyl, benzyl,
more preferably hydrogen, methyl or ethyl,
or $R^4$ and one of the radicals $R^5$ may together form a ring which includes the atoms to which $R^4$ and $R^5$ are bonded, this ring preferably comprising 5 to 8 carbon atoms,
$R^6$ and $R^7$=independently at each occurrence the same as $R^5$ and/or alkoxy, preferably methyl groups,
$R^{11}$=independently at each occurrence a saturated or unsaturated alkyl group having 1 to 24 carbon atoms, preferably 1 to 14 carbon atoms, and whose chain may be interrupted by oxygen and may further carry functional groups, such as, for example, carboxyl groups, optionally esterified with alcohols such as, for example, methanol, ethanol, propanol, butanol or hexanol, hydroxyl groups optionally esterified with acids such as acetic acid, butyric acid or (meth)acrylic acid and/or the polymers of (meth)acrylic acid, or an aryl group having 6 to 20 carbon atoms, or an alkaryl group having 7 to 30, preferably 7 to 20 carbon atoms,
being preferably a methyl, ethyl, hexyl, octyl, 2-ethylhexyl, phenyl, cresyl, tert-butylphenyl or benzyl group and/or an allyl group or a (poly)(meth)acrylic ester, more preferably a 2-ethylhexyl group or a tert-butylphenyl or benzyl group.

The fragments D, T and Q may also be described as follows:
D is a polyether radical PE with t being 2,
T is a polyether radical PE with t being 3 and
Q is a polyether radical with PE with t being 4.
PE is independently at each occurrence a polyether residue of the formula $-(D^A)_t-D^X$,
wherein t=2 to 4, preferably greater than 2 to less than 4, and
$D^X$ is a t-valent functional, saturated or unsaturated, linear or branched organic hydrocarbon residue which may comprise O, S, Si and/or N as heteroatoms, with each of the radicals $D^A$ being bonded covalently to the radical $D^X$,
the hydrocarbon residue preferably comprises 8 to 1500 carbon atoms,
the carbon chain of the hydrocarbon residue is preferably interrupted by oxygen atoms,
the hydrocarbon residue preferably comprises substituents containing silicon atom,
the substituents containing silicon atom are preferably alkoxysilyl groups,
the hydrocarbon residue interrupted by oxygen atoms is preferably a polyoxyalkylene residue, polyether residue and/or polyetheralkoxy residue,
or $D^X$ may be a singly or multiply fused phenolic group,
or more preferably $D^X$ may be a t-valent radical of a saccharide, (poly)urethane, perfluorinated polyetherol, siloxane, polyesterol, polyetherol or alcohol which is hydroxylated t times, preferably OH-functional polyethers, polyesters, polycarbonates, polyether esters or perfluorinated polyethers and copolymers thereof, more preferably OH-functional polyethers or polyesters, and where $D^4$ is a fragment of the formula (II)

formula (II)

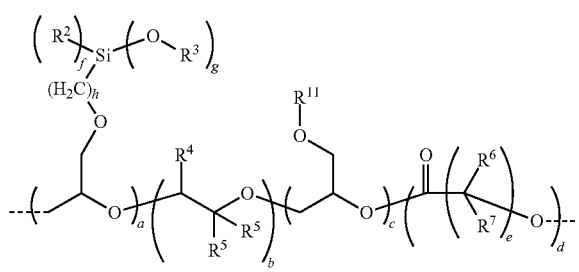

with b to h and $R^2$ to $R^7$ and $R^{11}$ defined as in formula (Ia), and a=0 to 1000, preferably 1 to 100 or greater than 1 to 100, more preferred 2 to 50, with the proviso that if M carries no substituents with alkoxysilyl groups or is itself not directly substituted by alkoxysilyl groups, the index a must be greater than or equal to 1.

Accordingly, the polyether residues D may be polyethers prepared starting with a dihydroxy-substituted compound. The polyether residues T may be a polyether prepared starting with a trihydroxy-substituted compound. The polyether residues Q may be polyether prepared starting with a tetrahydroxy-substituted compound. The fragment M may be a polyether prepared starting with a monohydroxy-substituted compound.

UR are, independently of one another, identical or different divalent residues of form where U is a —U—C(O)—NH group which is bonded via the nitrogen to $D^C$, and $D^C$ is a divalent substituted or unsubstituted hydrocarbon residue;

preferably $D^C$ is a hydrocarbon residue having 6-30 carbon atoms;

more preferably $D^C$ is an isophorone residue.

AP are, independently of one another, identical or different residues of the general formula (IIIa) or (IIIb)

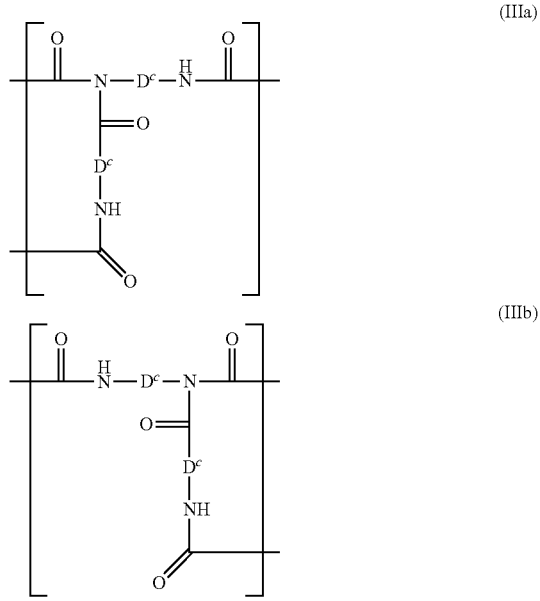

The fragment UR may be termed a urethane bridge. The fragment AP may be termed an allophanate bridge.

The residue $R^{11}$ may carry further functional groups such as, for example, (meth)acrylic acid and/or polymers of (meth) acrylic acid. Any hydroxyl groups present, therefore, may have been esterified with acrylic acid and/or methacrylic acid. The double bonds of the (meth)acrylic acid are polymerizable, for example radically, for example with UV induction.

The polymerization of the (meth)acrylic groups may take place after the preparation of the polyether. It may also be carried out with the alkoxylation products of the invention, with the products of the process of the invention, and also in accordance with the inventive use.

$D^X$ is a t-valent functional, organic hydrocarbon residue. A feature of the functionality is that it is capable of initiating a polymerization of alkylene oxides with ring opening, of acid esters with transesterification and/or of acid lactones with rung opening. In this sense it represents a starter compound. The polymerization may optionally take place catalytically. Serving as catalysts may be acids, bases and metal atom-containing complexes. It is preferred to use what are called DMC catalysts. This is subject to the customary rules of addition reaction that are known to the skilled person—for example, that the starter reacts preferably on the less-substituted side of the alkylene oxides or on the carbonyl carbon of the lactones. In the case of the formula (II), this corresponds to the left-hand side of the formula.

The OH functions of the polyethers react with the isocyanate functions to form urethanes. In the course of this reaction there are generally a series of secondary reactions (e.g. addition of an isocyanate group to a urethane unit to form the allophanate group), whose extent can be controlled through the choice of the reaction conditions.

Preferred alkoxylation products of the invention are those of the formula (I) in which the indices k and l are zero. Particularly preferred are alkoxylation products/polymers of the polyethers PE which are dihydroxy-functional. Particularly preferred are divalent polyethers PE which have been prepared from 3-glycidyloxypropyltriethoxysilane (GLYEO) and propylene oxide (PO) and optionally also ethylene oxide (EO) and/or glycidyl ethers and/or lactone. Especially preferred are dihydroxy-functional polyethers PE which have been prepared exclusively from GLYEO and PO or exclusively from GLYEO and PO and EO. The starter $D^X$ is preferably a polypropylene glycol.

Particularly preferred alkoxylation products of the formula (I) of the invention are those in which the fragment M has no alkoxysilyl and/or alkylsilyl groups.

Further particularly preferred are alkoxylation products of the invention which, based on the individual molecule, have on numerical average more than one alkoxysilyl group per group UR.

Further preferred are alkoxylation products of the formula (I) of the invention in which k, l and v=zero. Further preferred are alkoxylation products in which the index i is 2, the index j is 2 to 3 and the index u is 3 to 4.

EP 2 093 244 describes how alkoxysilanes which carry epoxide functions can be selectively alkoxylated advantageously in the presence of known double metal cyanide catalysts. The process claimed therein opens up the possibility for reproducibly performing the single and/or multiple alkoxysilyl-group modification of polyoxyalkylene compounds not only terminally but also within the sequence of oxyalkylene units. The disclosure content of EP 2 093 244 is considered in full to be a constituent part of the present description.

The products of the invention are preferably obtainable via an alkoxylation process using double metal cyanide catalysts (DMC catalysts). These catalysts, their preparation and use as alkoxylation catalysts, have been known since the 1960s and are set out for example in U.S. Pat. Nos. 3,427,256, 3,427,334, 3,427,335, 3,278,457, 3,278,458 or 3,278,459. Among the ever more effective types of DMC catalysts developed further in the subsequent years and described for example in U.S. Pat. Nos. 5,470,813 and 5,482,908, zinc cobalt hexacyano complexes are a special instance. By virtue of their extremely high activity, only small concentrations of catalyst are needed to prepare polyetherols, and hence there is no need, at the end of the alkoxylation procedure, for the workup stage—consisting of the neutralization, precipitation and isolation by filtration of the catalyst—that is necessary for conventional alkaline catalysts. The high selectivity of the DMC-catalysed alkoxylation is a reason why, for example, propylene oxide-based polyethers contain only very small fractions of unsaturated by-products.

Examples of further references include EP-A1-1 017 738, U.S. Pat. No. 5,777,177, EP-A1-0 981 407, WO 2006/002807 and EP-A1-1 474 464.

Examples of alkylene oxide compounds that can be used are ethylene oxide, 1,2-epoxypropane (propylene oxide), 1,2-methyl-2-ethoxypropane, epichlorohydrin, 2,3-epoxy-1-propanol, 1,2-epoxybutane (butylene oxide), 2,3-epoxybutane, 1,2-methyl-3-ethoxybutane, 1,2-epoxypentane, 1,2-methyl-3-ethoxypentane, 1,2-epoxyhexane, 1,2-epoxycyclohexane, 1,2-epoxyheptane, 1,2-epoxyoctane, 1,2-epoxynonane, 1,2-epoxydecane, 1,2-epoxyundecane, 1,2-epoxydodecane, styrene oxide, 1,2-epoxycyclopentane, 1,2-epoxycyclohexane, vinylcyclohexene oxide, (2,3-epoxypropyl)benzene, vinyloxirane, 3-phenoxy-1,2-epoxypropane, 2,3-epoxymethyl ether, 2,3-epoxyethyl ether, 2,3-epoxyisopropyl ether, 2,3-epoxy-1-propanol, (3,4-epoxybutyl)stearate, 4,5-epoxypentyl acetate, 2,3-epoxypropane methacrylate, 2,3-epoxypropane acrylate, glycidyl butyrate, methyl glycidate, ethyl-2,3-epoxybutanoate, 4-(trimethylsilyl)butane 1,2-epoxide, 4-(triethylsilyl)butane 1,2-epoxide, 3-(perfluoromethyl)propene oxide, 3-(perfluoroethyl)propene oxide, 3-(perfluorobutyl)propene oxide, 4-(2,3-epoxypropyl)morpholine, 1-(oxiran-2-ylmethyl)pyrrolidin-2-one. It is preferred to use ethylene oxide, propylene oxide and butylene oxide. It is particularly preferred to use ethylene oxide and propylene oxide.

Depending on the epoxide-functional alkoxylsilane used and on any other monomers that are employed, it is possible to prepare modified alkoxylation products (II), and also mixtures of any desired composition.

A non-conclusive collection of alkoxysilanes substituted by epoxide groups and able to be used alone or in mixtures with one another, or in combination with epoxide compounds, in the context of the invention, includes, for example, 3-glycidyloxypropyltrimethoxysilane, 3-glycidyloxypropyltriethoxysilane, 3-glycidyloxypropyltripropoxysilane, 3-glycidyloxypropyltriisopropoxysilane, bis(3-glycidyloxypropyl)dimethoxysilane, bis(3-glycidyloxypropyl)diethoxysilane, 3-glycidyloxyhexyltrimethoxysilane, 3-glycidyloxyhexyltriethoxysilane, 3-glycidyloxypropylmethyklimethoxysilane, 3-glycidyloxypropylethyldiethoxysilane.

For the purposes of the present invention, the compounds which supply the residue $R^1$ in the formula (Ia) are substances which form the start of the alkoxylation product to be prepared, particularly of the formula (Ia), which is obtained by the addition reaction, according to the invention, of epoxide-functional monomers and any further comonomers. The starter compound used in the process of the invention is preferably selected from the group of the alcohols, polyetherols or phenols. A particularly preferred starter compound used is a mono- or polyhydric polyether alcohol or alcohol. It is preferred to use mono- to tetrahydric polyether alcohol or alcohol.

Preferred OH-functional starter compounds $R^1$—H used, where the hydrogen is part of the hydroxyl group, are compounds having molar masses of 31 to 10 000 g/mol, more preferably 50 to 2000 g/mol, more particularly 60 to 80 g/mol. The starter compounds can be used in any desired mixtures with one another or as pure substance. It is also possible to use hydroxyl compounds substituted pendently with substituents containing alkoxylsilyl groups, or by alkoxylsilyl groups directly, such as the silyl polyethers described in EP 2093244, as starter compounds.

As starter compounds it is advantageous to use low molecular mass polyetherols having molar masses of 50 to 2000 g/mol, which have in turn been prepared beforehand by DMC-catalysed alkoxylation.

Suitability is possessed not only by compounds having aliphatic and cycloaliphatic OH groups but also by any desired compounds having OH functions. These include, for example, phenol, alkylphenols and arylphenols.

OH-functional starter compounds $R^1$—H which may be used advantageously are, for example, allyl alcohol, 2-allyloxyethanol, vinyl alcohol, ethanol, and also all of the isomers of propanol, of butanol, of pentanol, of hexanol, of heptanol, of octanol and of nonanol. Additionally it is possible to use fatty alcohols especially. Typical examples are capryl alcohol, 1-undecanol, lauryl alcohol, 1-tridecanol, Isotridecyl alcohol, myristyl alcohol, 1-pentadecanol, cetyl alcohol, palmoleyl alcohol, 1-heptadecanol, stearyl alcohol, isostearyl alcohol, oleyl alcohol, elaidyl alcohol, petroselinyl alcohol, linolyl alcohol, linolenyl alcohol, 1-nonadecanol, elaeostearyl alcohol, arachyl alcohol, 1-heneicosanol, gadoleyl alcohol, behenyl alcohol, erucyl alcohol and brassidyl alcohol and also their technical mixtures. Starter compounds which can be employed, in addition to the compound class of the oxo-process alcohols, which usually carry 2 to 4 methyl groups in the branches, also include those known as Guerbet alcohols, which are branched with an alkyl group in 2-position. Suitable Guerbet alcohols include 2-ethylhexanol, 2-butyloctanol, 2-hexyldecanol and/or 2-octyldodecanol. Other alcohols which can be used include cyclic alcohols—cyclopentanol, 1-methylcyclopentanol, cyclohexanol, furfuryl alcohol, and solketal. Other suitable alcohols are any mono-OH-terminal polyethers and/or polyalkylene oxides such as, for example, methyl-started or butyl-started polyethylene oxides or polypropylene oxides and/or their mixed oxides. Particular preference is given to using butanol, 2-ethylhexanol, nonanol, isononanol, 3,5,5-trimethylhexanol, decanol and isotridecyl alcohol or a polyether consisting of polypropylene oxide prepared starting from butanol, very preferably with $R_1$, being $C_4H_9O[CH_2CH(CH_3)O_x]$, and x=4 to 7, more preferably with x=5.3.

As di- to tetra-OH-functional starter compounds, of the formula $D^x$ with t=2 to 4, for example, it is preferred to use compounds having molar masses of 62 to 10 000 g/mol, preferably 92 to 7000 g/mol, more preferably 122 to 5000 g/mol, and very preferably 2000 to 4000 g/mol. The starter compounds can be used in any desired mixtures with one another or as pure substances. It is also possible to use hydroxyl compounds substituted pendently with substituents containing alkoxylsilyl groups, or by alkoxylsilyl groups directly, such as the silyl polyethers described in EP 2093244, as starter compounds.

As starter compounds it is advantageous to use low molecular mass polyetherols having molar masses of 62 to 2000 g/mol, which have in turn been prepared beforehand by DMC-catalysed alkoxylation.

Suitability is possessed not only by compounds having aliphatic and cycloaliphatic OH groups but also by any desired compounds having OH functions. These include, for example, phenol, alkylphenols and arylphenols, or else carbohydrates such as saccharides, for example; particularly suitable starter compounds are bisphenol A and novolaks.

The alkoxylation products of the invention can be obtained in a variety of ways. It is preferred to prepare the alkoxylation products of the invention by the process of the invention that is described below.

The process of the invention for preparing the alkoxylation products of the invention is distinguished by the fact that in a first reaction step (a) polyethers of the formula PE are reacted with diisocyanates and in a second reaction step (b) the product/product mixture from the first reaction step (a) is reacted with a molecule of the formula H-M. The polyethers of the formula PE have been described above. The molecules of the formula H-M are compounds containing hydrogen bonded to the fragment M which has been described above.

In the process of the invention it is preferred to use the diisocyanates in a molar excess over the polyethers PE.

With further preference, the polyethers PE in the process of the invention are selected such that in the product there are more alkoxysilyl groups than groups UR.

The two reactions (a) and (b) are preferably carried out at separate times from one another. In that case it is preferred first to react the polyethers PE with the diisocyanates. In this step, the stoichiometric proportions determine the number of UR fragments in the product. In the second reaction step (b), the isocyanate groups that have not been consumed by reaction are reacted with the molecule H-M.

The reaction with the molecule H-M corresponds to an endcapping process. The aim of this reaction step is to bring about the consumption, by reaction, of preferably all of the isocyanate groups.

In the process of the invention it is possible to use difunctional isocyanates selected from the group encompassing, for example: toluene 2,4-diisocyanate (TDI), diphenylmethane diisocyanate or methylenediphenyl diisocyanate (MDI), hexamethylene diisocyanate (HMDI), 2,2,4-trimethylhexane 1,6-diisocyanate (TMDI), polymeric diphenylmethane diisocyanate (PMDI), isophorone diisocyanate (IPDI), 4,4'-diisocyanatodicyclohexylmethane (H12MDI), the aliphatic products being preferred and isophorone diisocyanate (IPDI) being particularly preferred. Trifunctional isocyanates that can be used are selected from the group encompassing, for example: triphenylmethane triisocyanate, benzene 1,3,5-triisocyanate and toluene 2,4,6-triisocyanate.

Some of these isocyanates have stereocentres. Particular attention is drawn to the isomers of isophorone. All conceivable isomers are expressly included in the scope of this invention. Thus, for example, isophorone diisocyanate can be differentiated into a cis-isomer and a trans-isomer. Particular preference is given to isophorone diisocyanate comprising a cis/trans mixture of 5:1 to 1:5, preferably 3:1 to 1:3, more preferably 1:1. One particularly preferred, commercial product consists of a cis/trans mixture of 3:1. The use of commercial isophorone diisocyanate is preferred. Isophorone diisocyanate is available under other names, which are included as synonyms in the scope of this invention: 3-Isocyanatomethyl-3,5,5-trimethylcyclohexyl isocyanate, 5-isocyanato-1-(isocyanatomethyl)-1,3,3-trimethylcyclohexane, CA RN: 4098-71-9. A diversity of trade names is customary, these names frequently containing the names of the parent molecular isophorone, although other trade names are also familiar: e.g. Desmodur®I (BAYER), Isocur IPDI 22-200 (ISO-ELEKTRA), VESTANAT® IPDI (EVONIK INDUSTRIES), which are likewise included in the scope of the present invention. Customary specifications for isophorone diisocyanate are as follows: total chlorine content<400 mg/kg, hydrolysable chlorine<200 mg/kg, purity>99.5 weight %, refractive index $n^{25}{}_D$ 1.483 (DIN 51 423, part 2), NCO content 37.5-37.8 weight % (EN ISO 11 909/ASTM D 2572), and the commercial product is described as being colourless to pale yellow.

Isocyanates can oligomerize. Commercial products frequently contain greater or lesser amounts of such oligomers. These oligomers may be described, for example, by the following formulae:

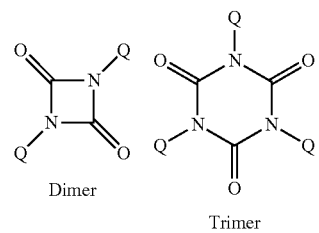

Dimer

Trimer

Q designates the residue of the isocyanate. To the skilled person it is possible to use the isocyanates identified above to derive the structures that are referred to here. The dimers and trimers are interpreted as being homodimers and homotrimers, respectively.

In the case of the abovementioned diisocyanates it would be possible here for structures to be formed which are capable of containing urethanes that correspond to UR, as analogous bridging elements, and which can be derived directly from the diisocyanate dimers shown.

The diisocyanate trimers may be capable of reacting with more than two polyethers PE. In that case it would be possible for bridging elements analogous to AP to form; these triurethanes can be derived in the same way from the structure shown above.

For the reaction of the molecules H-M and polyethers PE with diisocyanates it may be necessary to accelerate the reaction by catalysis. Catalysts which have been employed are the tin, bismuth and titanium catalysts well-known to the skilled person from urethane chemistry, such as dibutyltin laurate, dioctyltin diketonate, dibutyltin dilaurate, dioctyltin dilaurate, available for example under the trade name TIB KAT® 216 (Goldschmidt TIB/TIB Chemicals), dibutyltin diacetylacetonate, dibutyltin diacetate, dibutyltin dioctoate, or dioctyltin diacetylacetonate, Borchi® catalysts, bismuth oxides, bismuth carboxylate available for example under the trade name TIB KAT® 722 (Goldschmidt TIB/TIB Chemicals), bismuth methanesulphonate, bismuth nitrate, bismuth chloride, triphenylbismuth, bismuth sulphide, and also preparations with these catalysts, titanates, e.g. titanium(IV) isopropoxide, iron(III) compounds, e.g. iron(III) acetylacetonate, aluminium compounds, such as aluminium triisopropoxide, aluminium tri-sec-butoxide and other alkoxides, and also aluminium acetylacetonate.

Also suitable, furthermore, are zinc salts, such as zinc octoate, zinc acetylacetonate and zinc 2-ethylcaproate, or tetraalkylammonium compounds, such as N,N,N-trimethyl-N-2-hydroxypropylammonium hydroxide, N,N,N-trimethyl- N-2-hydroxypropylammonium 2-ethylhexanoate or choline 2-ethylhexanoate. Preference is given to the use of zinc octoate (zinc 2-ethylhexanoate), dioctyltin dilaurate, bismuth oxides, bismuth carboxylate, bismuth catalyst preparations and/or the tetraalkylammonium compounds, more preferably to the use of zinc octoate, dioctyltin dilaurate and/or bismuth carboxylate, and also preparations with bismuth catalysts.

The catalyst is used preferably in concentrations of 5-5000 ppm. The amount in which the catalyst is used may considerably influence the composition of the end product. For different catalysts it may therefore be sensible to select different use concentrations. For example, organotin catalysts can be used preferably in concentrations of 5-150 ppm, and bismuth carboxylates preferably in concentrations of 300-2000 ppm.

Alkoxylation products of the invention can be prepared/obtained with preference by any process suitable for obtaining alkoxylation products of the invention. Particularly preferred alkoxylation products of the invention are those which are preparable/obtainable and prepared/obtained by processes described below.

The present invention accordingly further provides processes preferably for preparing alkoxylation products. Processes described below are especially suitable for preparing alkoxylation products of the invention in general, and also, more particularly, for preparing alkoxylation products of the invention comprising the preferred embodiments described for the alkoxylation products of the invention.

The claimed process for preparing the final alkoxylation products may consist of a two-stage reaction sequence, in which case preferably in a first reaction step (a) polyethers of the formula PE are reacted with diisocyanates (as defined above) and in a second reaction step (b) the product of the first reaction step (a) is reacted with a molecule of the formula H-M.

In preferred processes of the invention for preparing alkoxylation products, the polyethers PE and the diisocyanates may react preferably in the presence of a catalyst. With preference it is possible to use diisocyanates in a molar excess over the polyethers PE.

In the process of the invention it is preferred to mix polyethers PE and diisocyanates with one another in reaction step (a). With preference the diisocyanates can be added to the polyethers PE. With preference the diisocyanates can be added to heated polyethers PE. Mixing is performed preferably at an elevated temperature, encompassing temperatures greater than 25° C., more preferably at temperatures of 40° C. to 100° C., very preferably at 60° C. to 80° C. With preference the reaction may take place in the presence of a catalyst, more preferably in concentrations of 5-5000 ppm. It may also be preferred for the catalyst to be added at the mixing temperature, encompassing temperatures greater than 25° C., more preferably at temperatures of 40° C. to 100° C., very preferably at 60° C. to 80° C. The mixture comprising diisocyanates and polyethers PE and also, preferably, catalyst is preferably stirred before and/or during and/or after the addition of individual components. Stirring for the purposes of this invention means any way in which a reaction mixture is commixed. Stirring may take place preferably at elevated temperature, encompassing temperatures greater than 25° C., more preferably at temperatures of 40° C. to 100° C., at 60° C. to 80° C. Stirring is preferably carried out throughout the reaction time. More preferably the mixture can be stirred for 15 to 90 minutes, very preferably 30 to 60 minutes, more particularly 45 minutes, preferably at the mixing temperature.

If desired it is possible to add to the reaction mixture, as particularly preferred components, additionally catalyst, more preferably in concentrations of 5-5000 ppm, based on the total concentration of all of the catalysts in the reaction mixture, and/or diisocyanates and/or polyethers PE.

With preference it is possible for the mixture to be subsequently heated further—or, if no heating has taken place beforehand, for the first time. With particular preference the mixture can be heated by 5° C. to 30° C., more preferably by 7° C. to 20° C., very preferably by 10° C. to 15° C. The reaction mixture can be heated preferably to 60 to 100° C., more preferably to 60 to 80° C. It may be especially preferable that the mixing temperature can be situated at 70° C.-80° C. and that this temperature can be maintained for subsequent process steps.

To the reaction mixture in reaction step (b) it is further preferred to add the molecule H-M. With preference a certain amount of the molecule H-M can be added at the elevated temperature. The molecule H-M can be added preferably at 60 to 80° C., more preferably at 65 to 75° C. With preference it is possible to carry out (further) stirring during and/or after the addition of the molecule H-M. In the case of particular embodiments it may be of advantage if a further addition of catalyst is made before or during the reaction with H-M. In the case of this further addition of catalyst, it is possible to add either the same catalyst used in the first reaction step, or a different catalyst. The mixture may be stirred preferably for several hours, preferably 1 to 8 hours, more preferably 1.5 to 4 hours, more particularly 3 hours, preferably at the elevated temperature. The steps of the process can be carried out in any desired order. In one particularly preferred embodiment, the order of the process steps is the above-recited order of their description.

The reaction products can be subsequently cooled, preferably to room temperature.

It is, however, also possible to supply further components to the reaction mixture, such as catalysts, PE and diisocyanates, and also, optionally, compounds H-M, and to continue the reaction. In the course of such continued reaction it is additionally possible, for example, to add one or more catalysts, which may be the same as or different from that or those catalyst(s) employed beforehand in reaction steps (a) and (b). Moreover, it is possible, for example, to add, additionally one or more compounds of the formula H-M, which may be the same as or different from the compound(s) H-M metered in beforehand. It is also additionally possible, for example, to add one or more diisocyanates, which may be the same as or different from the diisocyanate(s) used beforehand in reaction step (a).

As particularly preferred components it is possible to add catalyst to the reaction mixture, more preferably in concentrations of 5-5000 ppm, based on the total concentration of all catalysts in the reaction mixture, and/or to add diisocyanates and/or polyethers PE, preferably just catalyst. The components can be supplied simultaneously or in succession and/or else in portions, preferably in 2 to 12 portions, to the reaction mixture. In one preferred embodiment it is possible to supply catalyst and at least one further component selected from diisocyanates and/or polyethers PE alternately to the reaction mixture, and the total amount of the individual components can be subdivided in each case into 2 to 12 portions and optionally one portion of the selected component in each case is supplied alternately to the reaction mixture. If catalyst is supplied to the reaction mixture, it may be preferable to add the same catalyst as optionally added in the preceding reaction step, preferably in portions, or else to add one or more further catalysts different from the optional first catalyst, again preferably in portions. The addition of further components may be made preferably at elevated temperature, encompassing temperatures greater than 25° C., more preferably at temperatures of 40° C. to 100° C., at 60° C. to 80° C., and very preferably at a temperature which remains the same, encompassing temperature changes of 5° C. more or less, as in the preceding step. The reaction mixture is preferably stirred before and/or during and/or after the addition of further components, more preferably catalyst and/or diisocyanates and/or polyethers PE. The mixture may preferably be stirred for a number of hours, more preferably 1 to 8 hours, especially 1.5 to 4 hours. If desired, the addition of further components, preferably of catalyst, may be carried out one or more times, in other words, twice, thrice, four times, etc., in other words as often as desired, more preferably once, within the above-indicated temperature ranges and optionally under the cited stirring conditions.

Especially preferred in accordance with the invention are those processes which take place in the presence of a catalyst, more preferably in concentrations of 5-5000 ppm, and in which as a further component catalyst is added at least one further time, preferably in portions, more preferably in concentrations of 5-5000 ppm, based on the total concentration of all catalysts in the reaction mixture.

On account of their alkoxysilyl groups, which are sensitive to hydrolysis and have a tendency to undergo crosslinking, these alkoxylation products of the invention represent curable modified polymers or oligomers. Their crosslinking to solid thermoset end products, or else, depending on the choice of the crosslinking density or particular adjuvants, to elastomeric or thermoplastic end products, is accomplished in a simple way in the presence of water and, optionally, with addition of a catalyst. This catalyst may be, for example, an acid or a base or else a metal-containing compound. The pot life can be controlled—curtailed, for example—by variation, for example increasing in the temperature during the curing procedure. For example, through a variation in the fraction of alkoxysilane units in the modified polymer chain, it is possible to influence the crosslinking density and hence the mechanical and physicochemical properties profile of the cured modified polymers within wide limits.

Besides the alkoxylation product of the invention and/or the product of the process of the invention, of the formula (I), the compositions of the invention preferably comprise further adjuvants selected from the group of the plasticizers, fillers, solvents, emulsifiers, adhesion promoters, additives for modifying the flow behaviour, known as rheology additives, and at least one curing catalyst. If necessary, it is also possible for additives for chemical drying, and/or stabilizers against thermal and/or chemical exposures and/or exposures from ultraviolet and visible light, to be incorporated into the formulation.

Furthermore, the compositions may also comprise functional substances that are known per se, such as rheological additives, water scavengers, thixotropic agents, flame retardants, blowing agents or defoamers, deaerating agents, film-forming polymers, antimicrobial substances and preservatives, antioxidants, dyes, colourants and pigments, frost preventatives, fungicides, adhesion promoters and/or reactive diluents and also plasticizers and complexing agents, spraying assistants, wetting agents, vitamins, growth substances, hormones, active pharmacological ingredients, fragrances, light stabilizers, radical scavengers, UV absorbers and/or further stabilizers.

The alkoxylation products of the invention and the products of the process of the invention can be used alone or in a blend with an alkoxylation product prepared as per EP 2 093 244. In mixtures which comprise alkoxylation products corresponding to alkoxylation products prepared as per EP 2 093 244, preferably, the fraction of the alkoxylation products of the invention and/or of the products of the process of the invention is more than 25 weight %, preferably more than 50 weight % and more preferably more than 75 weight %, based on the total mass of the alkoxylation products.

The plasticizers are selected from the group of the phthalates, the polyesters, alkylsulphonic esters of phenol, cyclohexanedicarboxylic esters, or else of the polyethers, and their proportion in the formulation can be 0 to 90 weight %, preferably 2 to 70 weight %, more preferably 5 to 35 weight/0.

Fillers used may be precipitated or ground chalk, precipitated or ground silicates, precipitated or fumed silicas, glass powders, glass beads, hollow glass beads (known as bubbles), metal oxides, such as TiO, and $Al_2O_3$, for example, metal hydroxides, such as aluminium hydroxide, for example, wood flour, natural or precipitated barium sulphates, reinforcing fibres, such as glass fibres or carbon fibres, for example, wollastonites in long or short fibre form, cork, carbon black or graphite. The fillers are used preferably in a concentration of 0 to 90 weight %, based on the completed mixture, and concentrations of 5 to 70 weight % are particularly preferred. It is further advantageous to use hydrophobized fillers, since these products introduce relatively little water, and improve the storage stability of the formulations. Many of the stated fillers either can be hydrophobized subsequently or can be produced in hydrophobized form by a skilful process regime, or can even be hydrophobized by the alkoxylation products of the invention. The methods of hydrophobizing are diverse and are known to the skilled person.

The mixtures may comprise organic substances, preferably liquids and solvents. These solvents are used, for example, to lower the viscosity of the non-crosslinked mixtures, and they promote attachment onto the particle surface. Solvents contemplated include, in principle, all solvents and also solvent mixtures. Preferred examples of such solvents are ethers such as tert-butyl methyl ether, for example, esters, such as ethyl acetate, or butyl acetate or diethyl carbonate, for example, and also alcohols, such as methanol, ethanol and also the various regioisomers of propanol and of butanol, for example, or else glycol types selected specifically according to application. It is also possible for aromatic and/or aliphatic solvents, and also halogenated solvents, such as dichloromethane, chloroform, carbon tetrachloride, fluorinated hydrocarbons (FREON) and others, to be employed, and also inorganic solvents such as, for example, water, $CS_2$, supercritical $CO_2$, and others.

The rheology additives may be selected from the group of the amide waxes, obtainable for example from Cray Valley under the brand name Crayvallac®, hydrogenated vegetable oils and fats, fumed silicas, such as Aerosil® R202 or R805 (both of which can be purchased from Evonik) or Cab-O-Sil® TS 720 or TS 620 or TS 630 (sold by Cabot), for example. Depending on the desired flow behaviour, these additives are used in a fraction of 0 to 10 weight %, preferably with a fraction of 2 to 5 weight %, in the overall formulation. Chemical drying agents which can be used, alone or in mixtures, are vinyltrimethoxysilane (Dynasylan® VTMO, Evonik or Geniosil® XL 10, Wacker AG), vinyltriethoxysilane (Dynasylan® VTEO, Evonik or Geniosil® GF 56, Wacker), vinyltriacetoxysilane (Geniosil® GF 62, Wacker), N-trimethoxysilylmethyl O-methylcarbamate (Geniosil® XL 63, Wacker) N-dimethoxy(methyl)silylmethyl O-methyl-carbamate, N-methyl[3-(trimethoxysilyl)propyl]carbamate (Geniosil® GF 60, Wacker), vinyldimethoxymethylsilane (Geniosil® XL 12, Wacker), vinyltris(2-methoxyethoxy)-silane (Geniosil® GF 58, Wacker) bis(3-triethoxysilylpropyl) amine (Dynasylan® 1122, Evonik), bis(3-trimethoxysilylpropyl)amine (Dynasylan® 1124), N-dimethoxy(methyl) silylmethyl O-methylcarbamate (Geniosil® XL 65, Wacker) or oligomeric vinylsilanes such as, for example Dynasylan® 6490 and Dynasylan® 6498 (both of which can be purchased from Evonik). The use concentration is guided by the degree of stabilization and by the effectiveness of the drying agent, preferably with a fraction in the overall formulation of 0 to 5 weight %, more preferably with a fraction of 0.2 to 3 weight %. Furthermore, in addition or as an alternative to the chemical drying, it is possible to use a physical drying agent, such as, for example zeolites, molecular sieves, anhydrous sodium sulphate or anhydrous magnesium sulphate. Adhesion promoters used, in each case alone or in a mixture, are the substances known to the skilled person, principally compounds which carry alkoxysilyl groups and which additionally possess primary or secondary amine groups, vinyl groups, thiol groups, aryl groups or, alternatively, oxyrane groups, such as 3-aminopropyltrimethoxysilane (Dynasylan® AMMO (Evonik)), N-(2-aminoethyl)-3-aminopropyltrimethoxysilane (Dynasylan® DAMO (Evonik)), 3-mercaptopropyltrimethoxysilane (Dynasylan® MTMO, Evonik), 3-glycidyloxypropyltriethoxysilane (Dynasylan® GLYEO, Evonik) glycidyloxypropyl-trimethoxysilane (Dynasylan® GLYMO, Evonik), phenyltrimethoxysilane (Dynasylan® 9165 or Dynasylan® 9265, Evonik) or oligomeric amino/alkyl-alkoxysilanes such as, for example, Dynasylan® 1146 (Evonik). As stabilizers it is possible to use the products or product combinations known to the skilled person and comprising, for example Tinuvin® stabilizers (Ciba), examples being Tinuvin® 1130, Tinuvin® 292 or else Tinuvin® 400, also advantageously in combination. The amount in which they are used is guided by the degree of stabilization required. To the formulation it is additionally possible to admix co-crosslinkers for increasing mechanical hardness and reducing the flow tendency. Such co-crosslinkers are typically substances capable of providing 3, 4 or more crosslinkable groups. Examples in the context of this invention are 3-aminopropyltriethoxysilane, tetramethoxysilane or tetraethoxysilane.

As further components it is possible for the compositions of the invention to comprise preferably further, usually monomeric, silanes, hydroxyl-bearing siloxanes or solvents.

As further silanes it is possible here in principle to use all silanes, preferably with hydrolysable alkoxy groups, and more particularly silanes which carry amine groups or vinyl groups, and also those described in DE 10 2006 054155 or in WO 2005/003201.

The term monosilanol-forming compounds is used for those compounds which carry exactly one silanol group, or are capable of forming such compounds by reaction with moisture. Examples of compounds which carry silanol groups include the following structures: $(CH_3)_3SiOH$, $(CH_3CH_2)_3SiOH$, $(CH_3CH_2CH_2)_3SiOH$, $(C_6H_{10})_3SiOH$, $(C_6H_{10})_2CH_3SiOH$, $R_3Si-O-SiR_2-OH$ (where R may be a hydrocarbon or alternatively a siloxane), $(C_6H_{10})(CH_3CH_2)_2SiOH$, $(C_6H_{10})_2CH_3CH_2SiOH$.

Preferred compounds are those of the $R_3Si-OH$ type in which R is a methyl, ethyl, propyl, vinyl or phenyl group, the methyl group being particularly preferred. It is also possible to use all chlorosilanes and chlorosiloxanes that react with OH groups, such as $(CH_3)_3SiCl$, for example.

Examples of compounds which are capable of forming silanol-carrying compounds with moisture are (N,N-dimethylamino)triethylsilane, (N,N-dimethylamino)trimethylsilane, N,O-bis(trimethylsilyl)acetamide, N,O-bis(triethylsilyl)acetamide, N-(trimethylethylsilyl)acetamide, bistrimethylsilylurea, hexamethyldisilazane, 1,1,3,3,-tetramethyldisilazane, trimethylsilyl phenoxide, trimethylsilyl alkoxide (where the alkoxide originates from the group of the C1-C10 alcohols) and dimethylsilyldiethylamine, with the use of hexamethyldisilazane being particularly advantageous.

Additionally it is possible to use compounds of the formula $R_3Si-O-X$ in which X can stand for elements from the group of halogens, or alternatively for hydrocarbons which contain an acidic hydrogen atom. These hydrocarbons with acidic hydrogen atom may come from the group of the alcohols, preferably methanol, ethanol, propanol, butanol and isobutanol, or else may be derived from carboxylic acids, such as, for example, formic acid, acetic acid, propionic acid, succinic acid, lauric acid, palmitic acid, stearic acid, acrylic acid, methacrylic acid, oleic acid, linoleic acid, oxalic acid, maleic acid, adipic acid, benzoic acid, phthalic acid and terephthalic acid, and also the anhydrides of these acids, since the acid can likewise be formed from these anhydrides by ingress of moisture. Moreover, R may consist of primary or secondary amines. Examples that may be mentioned here include ammonia, methylamine, dimethylamine, ethylamine, diethylamine, propylamine, dipropylamine, butylamine and phenylamine. Further possibilities are acid amides and ketones.

When using the particularly preferred hexamethyldisilazane, but also when using many other silanol-forming compounds, it is advantageous to add to the reaction mixture an organic acid from the group of the carboxylic acids, since this significantly increases the yield of the reaction. Examples given here include the following: formic acid, acetic acid, propionic acid, succinic acid, lauric acid, palmitic acid, stearic acid, acrylic acid, methacrylic acid, oleic acid, linoleic acid, oxalic acid, maleic acid, adipic acid, benzoic acid, phthalic acid and terephthalic acid, with acetic acid, propionic acid, maleic acid and oleic acid being preferred. When HMDS is used together with the carboxylic acid that acts catalytically here, there is no competing reaction of the carboxylic acid with the HMDS for the OH function that is to be capped. The acids here react preferentially with the nitrogen of the HMDS. Particularly preferred is oleic acid, since under the reaction conditions it is of low volatility, causes virtually no discolouration and does not have an unpleasant odour. Additionally or alternatively it is also possible to catalyse the reaction by using a nitrogen base such as triethylamine, pyridine, aminopyridine or imidazole.

As catalysts for the crosslinking or polymerization of the compositions of the invention or for the chemical fixing thereof to particle surfaces or macroscopic surfaces, it is possible to use the known polyurethanization, allophanatization or biuretization catalysts, which are known per se to the skilled person, and/or the catalysts that are known from the literature and are commonly used for the hydrolysis and condensation of alkoxysilanes. These catalysts include compounds such as, for example, the commonly used organic tin compounds, such as dibutyltin dilaurate, dioctyltin dilaurate, dibutyltin diacetylacetonate, dibutyltin diacetate, dibutyltin dioctoate or dioctyltin diacetylacetonate, for example. In addition it is also possible to use zinc salts, such as zinc octoate, zinc acetylacetonate and zinc 2-ethylcaproate, or tetraalkylammonium compounds, such as N,N,N-trimethyl-N-2-hydroxypropyl ammonium hydroxide, N,N,N-trimethyl-N-2-hydroxypropylammonium 2-ethylhexanoate or choline 2-ethylhexanoate. It is preferred to use zinc octoate (zinc 2-ethylhexanoate) and the tetraalkylammonium compounds, more preferably zinc octoate. Furthermore, it is also possible to employ bismuth catalysts, examples being Borchi® catalysts, titanates, such as titanium(IV) isopropoxide, for example, iron(III) compounds, such as iron(III) acetylacetonate, for example, aluminium compounds, such as aluminium triisopropoxide, aluminium tri-sec-butoxide and other alkoxides, and also aluminium acetylacetonate, calcium compounds, such as calcium disodium ethylenediaminetetraacetate or calcium diacetylacetonate, or else amines, examples being triethylamine, tributylamine, 1,4-diazabicyclo[2,2,2]octane, 1,8-diazabicyclo[5.4.0]undec-7-ene, 1,5-diazabicyclo[4.3.0]non-5-ene, N,N-bis(N,N-dimethyl-2-aminoethyl)methylamine, N,N-dimethylcyclohexylamine, N,N-dimethylphenylamine, N-ethylmorpholine, etc. Organic or inorganic Brönsted acids as well, such as acetic acid, trifluoroacetic acid, methanesulphonic acid, p-toluenesulphonic acid or benzoyl chloride, hydrochloric acid, phosphoric acid and its monoesters and/or diesters, such as butyl phosphate, (iso)propyl phosphate, dibutyl phosphate, etc., are suitable catalysts. It is of course also possible to use combinations of two or more catalysts.

The compositions of the invention may also comprise so-called photolatent bases as catalysts, of the kind described in WO 2005/100482. By photolatent bases are meant preferably organic bases having one or more basic nitrogen atoms, which are initially in a blocked form and which release the basic form only after irradiation with UV light, visible light or IR radiation, by cleaving of the molecule. The content of the description and of the claims of WO 2005/100482 is hereby introduced as part of the present disclosure content.

The catalyst and/or the photolatent base is used in amounts of 0.001 to 5.0 weight %, preferably 0.01 to 1.0 weight % and more preferably 0.05 to 0.9 weight %, based on the sum total mass of the reaction components. The catalyst and/or the photolatent base can be added in one portion or else in portions or else continuously. It is preferred to add the total amount in one portion.

The compositions of the invention are suitable preferably for the bonding and/or sealing of particulate or sheet-like substrates. A further possible use is in the construction industry or in vehicle construction, for sealing and bonding construction elements and components, and for coating porous or non-porous, particulate or sheet-like substrates. As the basis of a curable composition, the alkoxylation products used in this invention can be used outstandingly for the coating and modification of surfaces and fibres. Further examples cited here are applications on metals, and especially on materials of construction such as iron, steel, stainless steel and cast iron, ferrous materials, aluminium, mineral substrates, such as stone, screed, mortar and concrete, ceramics, glasses, ceramic materials, especially based on solid metal oxides or non-metal oxides or carbides, aluminium oxide, magnesium oxide or calcium oxide, and also mineral substrates or organic substrates, polyesters, glass fibre-reinforced polyester, polyamide, textiles and fabrics made of cotton and polyester, and cork and/or wood. The composition may also be utilized for the binding, reinforcing and levelling of uneven, porous or fragmentary substrates, such as, for example, mineral substrates, chipboard and fibreboard panels comprising wood or cork, composite materials such as, for example, wood composites such as MDF (medium-density fibreboard) panels, WPC (wood plastic composite) articles, chipboard panels, cork articles, laminated articles, ceramics, and also natural fibres and synthetic fibres.

As a result of this broad spectrum of adhesion, they are also suitable for the adhesive bonding of materials combinations in the stated substrates. In that case it is not critical whether the surfaces are smooth or roughened or porous. Roughened or porous surfaces are preferential on account of the greater area of contact with the adhesive.

Accordingly, the alkoxylation products are able to serve, for example, as base materials for the production of adhesives, as reactive crosslinkers, as adhesion promoters and primers, and also binders for metals, glass and glass fibres/ glass fabrics, wood, wood-based materials, natural fibres, for the finishing and treatment of textile and non-textile sheetlike structures and fibres comprising natural and/or synthetic and also mineral raw materials and also, for example, cork, leather, paper, tissue, and silicatic and oxidic materials.

To illustrate the invention in an exemplary fashion, working examples are given below that stand as examples of the formulation of the products produced and for the spectrum of properties achievable in the formulation by virtue of the process of the invention.

Unless explicitly characterized, all figures relating to relative fractions (fractions in %) are stated as percent by weight.

EXAMPLES

1. General Methods and Materials

| | | |
|---|---|---|
| Diisononyl phthalate | Vestinol 9 (DINP) | Evonik Industries AG, Essen |
| Precipitated calcium carbonate | Socal U1S2 | Solvay Chemicals GmbH, Rheinberg |
| Titanium dioxide | Kronos 2310 | Kronos Titan GmbH, Leverkusen |
| | Dynasylan VTMO | Evonik Industries AG, Essen |
| | Dynasylan AMMO | Evonik Industries AG, Essen |
| | Irganox | BASF |
| | Tinuvin 292 | BASF |
| | Tinuvin 1130 | BASF |
| Dioctyltin diketonate | TIB KAT 223 | TIB Chemicals, Germany |
| | TIB KAT 722 | TIB Chemicals, Germany |
| | Aerosil R202 | Evonik Industries AG, Essen |
| | Dynasylan 1146 | Evonik Industries AG, Essen |
| 3-Glycidyloxypropyltriethoxysilane | GLYEO | Evonik Industries AG, Essen |
| Propylene oxide | PO | |
| Polypropylene oxide | Desmophen 2061.BD (PPG (2000 g/mol)) | Bayer Material Science |
| Polypropylene oxide | Acclaim 4200 (PPG (4000 g/mol)) | Bayer Material Science |
| Isophorone diisocyanate | Vestanat IPDI | Evonik Industries AG, Essen |
| n-Butyl isocyanate | | Lanxess |

2 Synthesis Examples:

The following polyethers containing alkoxysilyl groups were used, and were prepared in accordance with the process principle, set out in EP 2093244, of the DMC-catalysed alkoxylation of 3-glycidyloxypropyltriethoxysilane (GLYEO) with propylene oxide (PO):

Silyl Polyether SP-1:

Virtually colourless polyether, prepared starting from polypropylene glycol, with an average molar mass Mw of around 14 000 g/mol and with four-fold triethoxysilane functionality.

Chemical construction according to monomer metering:
PPG (2000 g/mol)+68 mol PO+a mixture of 4 mol GLYEO and 119 mol PO Silyl Polyether SP-2:

Virtually colourless polyether, prepared starting from polypropylene glycol, with an average molar mass Mw of around 14 000 g/mol and with two-fold triethoxysilane functionality.

Chemical construction according to monomer metering:
PPG (2000 g/mol)+18 mol PO+a mixture of 2 mol GLYEO and 180 mol PO

Example Procedure 1:

850 g of silyl polyether SP-1 were introduced and heated to 60° C., and 27.0 g of IPDI were added. Then 0.9 g of TIB KAT 722 was added. The mixture was stirred for 45 minutes. Thereafter 46.6 g of a polyether (A) of the general formula $C_4H_9O[CH_2CH(CH_3)O]_{5.3}H$ were added and the reaction mixture was stirred at 80° C. for a further three hours.

This gave a clear, colourless product having a viscosity of 48.9 Pa*s.

Example Procedure 2:

850 g of silyl polyether SP-1 were introduced and heated to 60° C., and 27.0 g of IPDI were added. Then 0.07 g of TIB KAT® 216 was added. The mixture was stirred for 45 minutes and subsequently heated to 70° C. Thereafter 46.6 g of a polyether (A) of the general formula $C_4H_9O[CH_2CH(CH_3)O]_{33}H$ were added and the reaction mixture was stirred at 70° C. for a further three hours. Then a further 0.02 g of TIB KAT® 216 were added in two equal-sized portions over the course of 30 minutes, followed by stirring at 70° C. for a further three hours.

This gave a clear, colourless product having a viscosity of 85 Pa*s.

Example Procedure 3:

850 g of silyl polyether SP-1 were introduced and heated to 70° C., and 27.0 g of IPDI were added. The temperature was held constant at about 70° C. throughout the reaction. 0.9 g of TIB KAT 722 was added. The mixture was stirred for 45 minutes. Thereafter 46.6 g of a polyether (A) of the general formula $C_4H_9O[CH_2CH(CH_3)O]_{5.3}H$ were added and the reaction mixture was stirred for a further three hours.

This gave a clear, colourless product having a viscosity of 58 Pa*s.

In accordance with Example Procedure 1, the further syntheses were carried out under identical conditions, with the quantities shown in Table 1. All of the products of Examples 1 to 6 were clear and colourless.

TABLE 1

Synthesis examples

| Example | Procedure | Silyl polyether | Initial mass of silyl polyether [g] | Initial mass of IPDI [g] | Catalyst | Initial mass [g] | Initial mass of A [g] | Viscosity [Pa*s] |
|---|---|---|---|---|---|---|---|---|
| 1 | 1 | SP-1 | 850 | 27 g | TIB KAT 722 | 0.9 g | 46.6 g | 48.9 |
| 2 | 1 | SP-1 | 800 | 27.9 | TIB KAT 722 | 0.9 | 52.7 | 34.5 |
| 3 | 1 | SP-1 | 830 | 34.3 | TIB KAT 722 | 0.9 | 72.9 | 25.6 |
| 4 | 1 | SP-2 | 865 | 27.5 | TIB KAT 722 | 0.9 | 47.5 | 111 |
| 5 | 1 | SP-2 | 855 | 26.9 | TIB KAT 722 | 0.9 | 56.3 | 83.1 |
| 6 | 1 | SP-2 | 740 | 30.5 | TIB KAT 722 | 0.8 | 65.0 | 51.2 |
| 7 | 2 | SP-1 | 135 | 5.1 | TIB KAT 216 | 0.008 | 10.3 | 22.9 |
| 8 | 2 | SP-1 | 269 | 10.2 | TIB KAT 216 | 0.018 | 20.6 | 24.4 |
| 9 | 3 | SP-1 | 500 | 27.9 | TIB KAT 722 | 0.9 | 52.7 | 40.5 |

Comparative Example C1:

2525 g of silyl polyether SP-1 were introduced and heated to 60° C., and 35.8 g of n-butyl isocyanate were added. Then 2.56 g of TIB KAT 722 were added. The mixture was stirred for 4 hours. This gave a clear, colourless product having a viscosity of 7-9 Pa*s.

Comparative Example C2:

2555 g of silyl polyether SP-2 were introduced and heated to 65° C., and 36.2 g of n-butyl isocyanate were added. Then 2.59 g of TIB KAT 722 were added. The mixture was stirred for 4 hours. This gave a clear, colourless product having a viscosity of 9-12 Pa*s.

3 Compositions:

Two samples each of synthesis examples S1 to S6, and also of Comparative Examples C1 and C2, are processed in accordance with the instructions to form preparation ZA and ZB.

Preparation ZA:

All of the percentages should be understood here to be parts by weight of the total formulation.

Composition:

The compositions consist of the respective aforementioned product of the invention at 25.9%, precipitated calcium carbonate at 51.1%, diisononyl phthalate at 18.1%, titanium dioxide at 0.5%, Dynasylan VTMO at 1.1%, Dynasylan AMMO at 1.4%, Irganox at 0.3%, Tinuvin 292 and Tinuvin 1130 each at 0.6%, and TIB KAT 223 at 0.4%.

The components of the stated formulations are incorporated in accordance with the methods known to the skilled person, it being necessary to place particular value on the exclusion of moisture and the avoidance of air inclusions when formulating.

As an example, the process of formulating on the laboratory scale in a mixer (Speedmixer DAC 600 FVZ (Hausschild)) may be stated. Formulating this composition in mixers on the pilot scale and production scale is of course also possible. The addition sequences and mixing times may each be adapted to the technical requirements. The process set out by way of example below is therefore only one possibility for the preparation of the curable composition.

The product of the invention, precipitated calcium carbonate, diisononyl phthalate and titanium dioxide are weighed out into a 400 ml PP beaker suitable for the mixing assembly, and are roughly predispersed using a spatula. The mixture is then mixed in the Speedmixer at 2300 1/min for 4 minutes. After the material has cooled to below 55° C., the two Dynasylan products (VTMO and AMMO) are added and are incorporated by mixing at 2300 1/min for 1 minute. Then Irganox and the two Tinuvin products (1130 and 292) are weighed out and are mixed in at 2300 1/min for 1 minute. Before the catalyst can be added, the temperature of the material ought to be below 55° C. again, in order to ensure trouble-free handling of the material under laboratory conditions. Lastly the TIB KAT 223 is added and is mixed in at 2300 1/min for 30 seconds. The composition is subsequently transferred into a euro cartridge, and sealed with the piston that fits the cartridge, and with closures, and this cartridge filled with the composition is stored at room temperature for at least 12 hours but not more than 3 days, prior to its further use.

Preparation ZB:

The compositions consist of the respective aforementioned product of the invention according to Example 1 at 36.8%, precipitated calcium carbonate at 44.8%, diisononyl phthalate at 11.0%, titanium dioxide at 0.4%, Aerosil 8202 at 3.5%, Dynasylan VTMO at 1.0%, Dynasylan 1146 at 1.7%, Irganox at 0.5%, and TIB KAT 223 at 0.4%.

The components of the stated formulations are incorporated in accordance with the methods known to the skilled person, it being necessary to place particular value on the exclusion of moisture and the avoidance of air inclusions when formulating.

As an example, the process of formulating on the laboratory scale in a mixer (Speedmixer DAC 600 FVZ (Hausschild)) may be stated. Formulating this composition in mixers on the pilot scale and production scale is of course also possible. The addition sequences and mixing times may each be adapted to the technical requirements. The process set out by way of example below is therefore only one possibility for the preparation of the curable composition.

The product of the invention, precipitated calcium carbonate, diisononyl phthalate and titanium dioxide are weighed out into a 400 ml PP beaker suitable for the mixing assembly, and are roughly predispersed using a spatula. The mixture is then mixed in the Speedmixer at 2300 1/min for 4 minutes. In the next step, the Aerosil 8202 is weighed out into the beaker and mixed in (2 minutes, mixer speed in this period rising from 800 1/min to 2300 1/min). After the material has cooled to below 55° C., the two Dynasylan products (VTMO and 1146) are added and are incorporated by mixing at 2300 1/min for 1 minute. Subsequently the Irganox is weighed in and is mixed in at 2300 1/min for 1 minute. Before the catalyst can be added, the temperature of the material ought to be less than 55° C. again, in order to ensure trouble-free handling of the material under laboratory conditions. Lastly the TIB KAT 223 is added and is mixed in at 2300 1/min for 30 seconds. The composition is subsequently transferred into a euro cartridge, and sealed with the piston that fits the cartridge, and with closures, and this cartridge filled with the composition is stored at room temperature for at least 12 hours but not more than 3 days, prior to its further use.

4. Use Examples

Determination of the Curing Layer:

To determine the through-cure characteristics of preparations A and B, 2 heaps from the cartridge, having a diameter and a height of at least 3 cm, are applied to a moisture-tight sheet. The heaps ought as far as possible to be coherent and to have an extremely smooth surface. The ideal is a round shape to the heap, with flanks that drop as steeply as possible.

After 24 hours and 7 days, one heap in each case is parted from the sheet, the portion that is still paste-like is removed, and the layer thickness of the cured composition is determined using a millimetre measure.

TABLE 2

Thickness of the curing layers as per Example 4

| | Curing 24 h layer thickness [mm] | Curing 7 days layer thickness [mm] |
|---|---|---|
| S1/ZA | 2 | 7 |
| S2/ZA | 2 | 6 |
| S3/ZA | 3 | 8 |
| S4/ZA | 3 | 12 |
| S5/ZA | 2 | 9 |
| S6/ZA | 2 | 7 |
| S1/ZB | 3 | 12 |
| S2/ZB | 3 | 12 |
| S3/ZB | 4 | 10 |
| S4/ZB | 0 | 11 |
| S5/ZB | 2 | 14 |
| S6/ZB | 2 | 12 |

The results in the table show that all of the preparations have cured sufficiently after 7 days.

Testing of Tensile Specimens:

Preparations A and B are introduced into a coating bar with slot dimensions of 2 mm, and are applied to a polyethylene sheet. After the bar-coated layer has cured, after 7 days at 23° C. and 50% relative humidity, tensile specimens conforming to DIN 53504-S2 are punched from this cured layer with the aid of a cutter and a toggle press.

Prior to the commencement of testing, the thickness of each of the rod-shaped tensile specimens manufactured in compliance with DIN 53504-S2 was measured, to take account of the effective cross-sectional area. The tensile specimens were clamped into a roller clamp on a universal testing machine (Schmidt) and tested at a tensile rate of 200 mm/min. The breaking stress is understood to be the stress (force per unit area) when the tensile specimen breaks. The elongation at break is understood to be the extension of the sample (elongation), as a percentage of the original length, when the tensile specimen breaks.

TABLE 3

Results of the testing of the tensile specimens in accordance with Example 4

| | Breaking stress [MPa] | Elongation at break [%] |
|---|---|---|
| S1/ZA | 1.6 | 56 |
| S2/ZA | 1.7 | 67 |
| S3/ZA | 1.6 | 64 |
| S4/ZA | 1.7 | 189 |
| S5/ZA | 1.7 | 196 |
| S6/ZA | 1.4 | 170 |
| S1/ZB | 2.1 | 39 |
| S2/ZB | 1.8 | 36 |
| S3/ZB | 1.7 | 36 |

TABLE 3-continued

Results of the testing of the tensile specimens in accordance with Example 4

| | Breaking stress [MPa] | Elongation at break [%] |
|---|---|---|
| S4/ZB | 1.9 | 105 |
| S5/7R | 2.0 | 126 |
| S6/ZB | 1.8 | 121 |
| C1/ZB | 1.2 | 53 |
| C2/2A | 0.6 | 196 |

The results of Table 3 show that the compositions of the invention can be used after curing to give products which possess a significantly improved breaking stress relative to the prior art. In these cases, the elongation at break can be adjusted over a wide range, depending on the compounds of the invention that are used and on the compositions that are prepared.

Testing of Adhesive Bonds:
Tensile Shear Bonds

Preparations A and B are applied directly from the cartridge to the similar materials to be bonded. Use was made in each case of two stainless steel substrates of steel grade 1.4301 (designated according to the steel code), of ABS polymer and, as a wood substrate, of beech (all of the test specimens were purchased from Rocholl). The bonded area in all cases was 500 mm², the layer thickness of the bond in all cases was more than 0.5 mm and less than 2.0 mm.

After curing under standard conditions (23° C. and 50% relative humidity), the tensile shear bonds were clamped into a jaw clamp on a universal testing machine, and pulled apart to fracture at 10 mm/min. Table 4 lists the stresses on the sample when the adhesive bond broke.

TABLE 4

Testing of the tensile shear bonds according to Example 4

| | V2A steel bond Breaking stress [MPa] | ABS bond Breaking stress [MPa] | Beech bond Breaking stress [MPa] |
|---|---|---|---|
| S1/ZA | 1.9 | 0.3 | 1.7 |
| S2/ZA | 1.8 | 0.3 | 1.6 |
| S3/ZA | 1.6 | 0.3 | 1.7 |
| S4/ZA | 1.6 | 0.2 | 1.7 |
| S5/ZA | 1.4 | 0.2 | 1.3 |
| S6/ZA | 1.3 | 0.2 | 1.2 |
| S1/ZB | 2.2 | 0.3 | 2.2 |
| S2/ZB | 2.0 | 0.3 | 2.1 |
| S3/ZB | 1.8 | 0.3 | 2.0 |
| S4/ZB | 1.8 | 0.3 | 1.6 |
| S5/ZB | 1.7 | 0.3 | 1.7 |
| S6/ZB | 1.6 | 0.4 | 1.7 |
| C1/ZB | 1.5 | 0.2 | 1.6 |
| C2/ZA | 0.9 | 0.2 | 1.0 |

The results in Table 4 show that the breaking stresses of the adhesive bonds, using the compositions according to the invention, are at least as high as those of the comparative compositions.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. Alkoxylation products comprising structural elements of the formula (I):

$$M_i D_j T_k Q_l UR_u AP_v \qquad \text{formula (I)};$$

wherein:

M, D, T and Q are linked not to one another but instead with one another via the groups UR and/or AP, and the groups UR and AP are not linked to one another;

i=2 to 16;

j=1 to 10;

k=0 to 6;

l=0 to 4;

j+k is greater than or equal to 2;

u=2 to 17; and v=0 to 6;

where:

M independently at each occurrence is a hydrocarbon radical, with no alkoxysilyl and/or alkylsilyl groups, which carries an oxygen radical and has a minimum numerical molar mass of 88 g/mol, and which may be further substituted and optionally be interrupted by heteroatoms;

D independently at each occurrence is a polyether radical PE with t being 2;

T independently at each occurrence is a polyether radical PE with t being 3;

Q independently at each occurrence is a polyether radical PE with t being 4;

UR is a divalent radical of the form —U-D$^c$-U—, where U is a —C(O)—NH group which is bonded via the nitrogen to D$^c$, and D$^c$ is a divalent hydrocarbon radical;

PE is a polyether residue of the formula $-(D^4)_t$-$D^x$;

where t=2 to 4;

where D$^x$ is a t-valent functional, saturated or unsaturated, linear or branched organic hydrocarbon residue which contains O, S, Si, and/or N as heteroatoms; and where D$^4$ is a fragment of the formula (II):

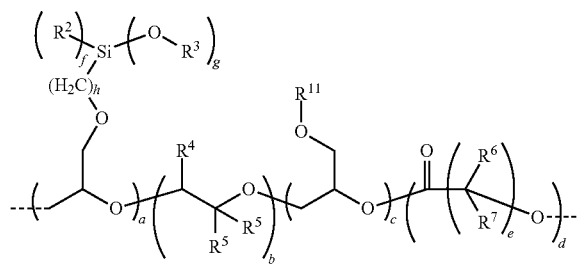

formula (II)

wherein:

R²=independently at each occurrence can be an alkyl group having 1 to 8 carbon atoms; and R³=independently at each occurrence an alkyl group having 1 to 8 carbon atoms;

wherein:

R⁴ and R⁵ are:

R⁴=independently at each occurrence a hydrogen radical or an alkyl group having 1 to 8 carbon atoms; and R⁵=independently at each occurrence a hydrogen radical, an alkyl group having 1 to 20 carbon atoms or an aryl or alkaryl group; or R⁴ and one of the radicals R⁵ may together form a ring which includes the atoms to which R⁴ and R⁵ are bonded;

wherein:

R⁶ and R⁷=independently at each occurrence the same as R⁵ and/or alkoxy; and

R¹¹=independently at each occurrence a saturated or unsaturated alkyl group having 1 to 24 carbon atoms, whose chain may be interrupted by oxygen and may further carry functional groups, or an aryl group having 6 to 20 carbon atoms, or an alkaryl group having 7 to 20 carbon atoms;

wherein:

a=1 to 1000;

with the proviso that if M carries no substituents with alkoxysilyl groups or is itself not directly substituted by alkoxysilyl groups, the index a must be greater than or equal to 1;

b=0 to 1000;

c=0 to 1000; and d=0 to 1000;

with the proviso that the groups having the indices a, b, c and d are freely permutable over the molecular chain; and wherein:

e=1 to 10;

g+f=3 and g is at least 1; and h=0 to 10;

with the proviso that the different monomer units, both of the fragments having the indices a, b, c, and d, and of the polyoxyalkylene chain of the substituent R¹, may be constructed in blocks with one another or else may be subject to a statistical distribution, and, moreover, are freely permutable with one another; and AP are, independently of one another, identical or different residues of the general formula (IIIa) or (IIIb):

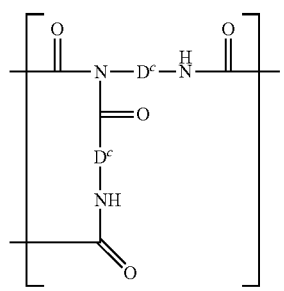

(IIIa)

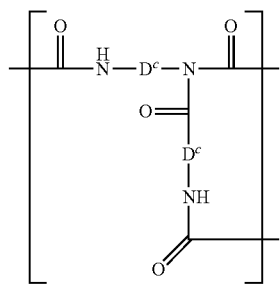

(IIIb)

2. The alkoxylation products according to claim 1; wherein, in formula (II), b=1 to 500.

3. The alkoxylation products according to claim 1; wherein k and l are zero.

4. The alkoxylation products according to claim 1; wherein M is a radical of the formula (Ia):

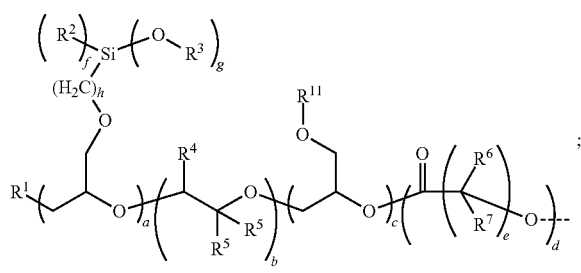

formula (Ia)

where:

R¹=independently at each occurrence a saturated or unsaturated, linear or branched organic hydrocarbon residue which may contain O, S and/or N as heteroatoms;

R²=independently at each occurrence an alkyl group having 1 to 8 carbon atoms; and R³=independently at each occurrence an alkyl group having 1 to 8 carbon atoms;

where:

R⁴ and R⁵ are:

R⁴=independently at each occurrence ahydrogen radical or an alkyl group having 1 to 8 carbon atoms; and R⁵=independently at each occurrence a hydrogen radical, an alkyl group having 1 to 20 carbon atoms or an aryl or alkaryl group; or R⁴ and one of the radicals R⁵ may together form a ring which includes the atoms to which R⁴ and R⁵ are bonded, where:

R⁶ and R⁷=independently at each occurrence the same as R⁵ and/or alkoxy; and

R¹¹=independently at each occurrence a saturated or unsaturated alkyl group having 1 to 24 carbon atoms, whose chain may be interrupted by oxygen and may further carry functional groups, or an aryl group having 6 to 20 carbon atoms, or an alkaryl group having 7 to 20 carbon atoms;

where:
   a=0;
      with the proviso that the index a in formula (II) must be greater than or equal to 1;
   b=1 to 1000;
   c=0 to 1000; and
   d=0 to 1000;
   with the proviso that the groups having the indices a, b, c and d are freely permutable over the molecular chain; and
where:
   e=1 to 10;
   g+f=3 and g is at least 1; and
   h=0 to 10;
with the proviso that the different monomer units, both of the fragments having the indices a, b, c, and d, and of the polyoxyalkylene chain of the substituent $R^1$, may be constructed in blocks with one another or else may be subject to a statistical distribution, and, moreover, are freely permutable with one another.

5. The alkoxylation products according to claim 1;
   wherein, based on the individual molecule, the alkoxylation products have on numerical average more than one alkoxysilyl group per group UR.

6. A process for preparing alkoxylation products according to claim 1, comprising:
   a first reaction step (a) where polyethers of the formula PE are reacted with diisocyanates; and
   a second reaction step (b) where the product of the first reaction step (a) is reacted with a molecule of the formula H-M;
   PE and M are as defined in claim 1.

7. The process according to claim 6;
   wherein the diisocyanates are used in a molar excess over the polyethers PE.

8. The process according to claim 6;
   wherein the polyethers PE are selected such that in the product there are more alkoxysilyl groups than groups UR.

9. The process according to claim 6;
   wherein, after the first reaction step (a) or after both the first and second reaction steps (a) and (b), at least one further component is added, the further component being selected from the group consisting of:
   catalysts, polyethers PE, diisocyanates, and molecules of the formula H-M.

10. A composition comprising:
    alkoxylation products according to claim 1.

11. The composition according to claim 10, further comprising:
    at least one curing catalyst.

12. The composition according to claim 10;
    wherein the alkoxylation products are in the form of a solution, emulsion, dispersion, or suspension.

13. The composition according to claim 10, further comprising:
    at least one adjuvant selected from the group consisting of: diluents, catalysts, plasticizers, fillers, solvents, emulsifiers, adhesion promoters, rheology additives, chemical drying additives, stabilizers against thermal and/or chemical exposures and/or against exposures to ultraviolet and visible light, thixotropic agents, flame retardants, blowing agents, defoamers, deaerating agents, film-forming polymers, antimicrobial and preservative substances, antioxidants, dyes, colourants, pigments, frost preventatives, fungicides, reactive diluents, complexing agents, wetting agents, co-crosslinkers, spraying assistants, vitamins, growth substances, hormones, active pharmacological ingredients, fragrances, and radical scavengers.

* * * * *